(12) United States Patent
Levy et al.

(10) Patent No.: US 8,518,914 B2
(45) Date of Patent: Aug. 27, 2013

(54) HMG-COA REDUCTASE AND FARNESYL-PYROPHOSPHATE SYNTHASE INHIBITORS FOR THE TREATMENT OF CONDITIONS RELATED TO PRENYLATED PROTEINS IN CELLS

(75) Inventors: Nicolas Levy, Marseilles (FR); Pierre Cau, Puyricard (FR); Carlos Lopez-Otin, Oviedo (ES)

(73) Assignees: Universite de la Mediterranee AIX-Marseille II, Marseilles (FR); Association Francaise Contre les Myophathies (AFM), Paris (FR); Assistance Publique Hopitaux de Marseille, Marseilles (FR); Universidad de Oviedo, Oviedo (ES)

( * ) Notice: Subject to any disclaimer, the term of this patent is extended or adjusted under 35 U.S.C. 154(b) by 92 days.

(21) Appl. No.: 12/307,220

(22) PCT Filed: Jul. 5, 2007

(86) PCT No.: PCT/FR2007/001144
§ 371 (c)(1),
(2), (4) Date: Sep. 22, 2009

(87) PCT Pub. No.: WO2008/003864
PCT Pub. Date: Jan. 10, 2008

(65) Prior Publication Data
US 2010/0120720 A1    May 13, 2010

(30) Foreign Application Priority Data

Jul. 5, 2006  (FR) ..................... 06 06097

(51) Int. Cl.
*A61K 31/66* (2006.01)
*A61K 31/21* (2006.01)

(52) U.S. Cl.
USPC ..................... 514/108; 514/510; 514/548

(58) Field of Classification Search
None
See application file for complete search history.

(56) References Cited

FOREIGN PATENT DOCUMENTS

| EP | 1 127 573 A | 8/2001 |
| EP | 1127573 A1 * | 8/2001 |

OTHER PUBLICATIONS

Gordon et al., "Reduced Adiponectin and HDL Cholesterol without Elevated C-Reactive Protein: Clues to the Biology of Premature Atherosclerosis in Hutchinson-Gilford Progeria Syndrome", J. Pediatrics, 2004, 146(3): 336-341.*
Fong et al., "A Protein Farnesyltransferase Inhibitor Ameliorates Disease in a Mouse Model of Progeria", Science, 2006, 311: 1621-1623 ("Fong").*
Toth et al., "Blocking Protein Farnesyltransferase Improves Nuclear Shape in Fibroblasts from Humans with Progenoid Syndromes", PNAS, 2005, 102(36): 12873-12878.*
Beek et al., "Farnesyl Pyrophosphate Synthase is the Molecular Target of Nitrogen-Containing Bisphosphonates", Biochemical and Biophysical Research Communications, 1991, 264, 108-111.*
Fong et al.; "A protein farnesyltransferase inhibitor ameliorates disease in a mouse model of progeria" Science; vol. 311, Mar. 17, 2006; pp. 1621-1623.
Gordon L. B. et al.; "Reduced adiponectin and HDL cholesterol without elevated C-reactive protein: Clues to the biology of premature atherosclerosis in Hutchinson-Gilford Progeria Syndrome"; Journal of Pediatrics, Mosby-Year Book; St. Louis, MO, US; vol. 146; No. 3; Mar. 2005; pp. 336-341.
Ignacia Varela et al., Combined Treatment With Statins and Aminobisphonates Extends Longevity in a Mouse Model of Human Premature Aging; published online Jun. 29, 2008, pp. 1-6; Supplementary Information 11 pages.
Leslie B. Gordon et al; Clinical Trial of a Farnesyltransferase Inhibitor in Children with Hutchinson—Gilford Progeria Syndrome, Oct. 9, 2012, vol. 109, No. 41;pp. 16666-16671, PNAS.

* cited by examiner

*Primary Examiner* — Sreeni Padmanabhan
*Assistant Examiner* — Svetlana M Ivanova
(74) *Attorney, Agent, or Firm* — Arent Fox LLP (57) ABSTRACT

The invention relates to the use of a hydroxymethylglutaryl-coenzyme A (HMG-CoA) reductase inhibitor and of a farnesyl-pyrophosphate synthase inhibitor, or of one of their associated physiologically acceptable salts, in the preparation of a composition, particularly a pharmaceutical composition, for use in the treatment of human or animal, pathological or nonpathological situations related to the accumulation and/or the persistence of prenylated proteins in cells, such as during progeria (Hutchinson-Gilford syndrome), restrictive dermopathy or physiological aging.

5 Claims, 5 Drawing Sheets

HMG-COA REDUCTASE AND FARNESYL-PYROPHOSPHATE SYNTHASE INHIBITORS FOR THE TREATMENT OF CONDITIONS RELATED TO PRENYLATED PROTEINS IN CELLS

CROSS-REFERENCE TO RELATED APPLICATION

This application is a National Stage entry of International Application No. PCT/FR2007/001144 filed Jul. 5, 2007, the disclosure of the prior application is hereby incorporated in its entirety by reference.

BACKGROUND OF THE INVENTION

The present invention lies in the field of the treatment of conditions, pathological or not, related to the accumulation and/or persistence in cells of prenylated proteins.

The nucleus of eukaryotic cells is delimited by a double membrane with pores in it, the nuclear envelope, which controls the molecular exchanges between the two nuclear and cytoplasmic compartments. This envelope partially isolates the content of the nucleus, that is to say the genetic material and all the enzymatic machinery necessary for the functions of the nuclear genome.

The nucleus envelope consists of two concentric membranes, the external membrane, in continuity with the endoplasmic reticulum, and the internal membrane. The latter is bordered on its internal face by a dense fibrillar mesh called the nuclear lamina. This is a protein lattice composed essentially of lamin polymers and associated proteins. In vertebrates, there are two sub-classes of lamins: type A lamins (lamins A and C), and type B lamins (lamins B1, B2 and B3), which all participate in the production of the lamina. The latter is held in place by association with other proteins, fixed to the internal membrane of the nuclear envelope (for journal, Gruenbaum et al 2005).

Lamins are proteins in the form of filaments belonging to the family of intermediate filaments (type V), which all have a common structure: a short N-terminal globular segment (the head) separated from another C-terminal globular segment (the tail) by a long central domain organised in several alpha helixes (the rod domain). The globular tail contains in particular a nuclear location signal (NLS) allowing addressing of the nucleus after synthesis. The central domain allows the association of two parallel lamin molecules and their organisation in filaments by the association of dimers in opposite orientations. This structure confers very resistant mechanical properties on them.

Only the A-type lamin and the B-type lamins undergo maturation after the synthesis of a precursor (Gruenbaum et al 2000). The C-type lamin is directly synthesised in its mature form.

The precursor of the A-type lamin and the B-type lamins terminates in a chracteristic CaaX unit (C is a cystein, a an amino acid with a non-charged aliphatic chain and X any amino acid, here a methionine, Levy & Cad 2003).

The C-terminal CaaX unit allows the fixing of a fatty acid (in general a C15 fatty acid, farnesyl) by virtue of a farnesyl-transferase. This prenylation (the farnesyl unit derives from a C5 base aliphatic unit called isoprenoid) enables the prelamins to be inserted in the membrane of the endoplasmic reticulum after their synthesis in cytosol. They undergo therein the action of an endoprotease, itself inserted in the envelope membrane of the reticulum and whose active site is cytosolic. The specific endoprotease of the prelamin A is Face1 (or ZMPSTE24 (Zinc Metallo-Protease homologue of yeast STE24), while Face2 (or Rce1, Ras-converting enzyme) is specific to the B prelamins. These enzymes catalyse the hydrolysis of the peptide bond between the cysteine and the following amino acid (aliphatic), shortening the prelamins by 3 amino acids. The carboxyl end of the farnesylated cysteine is then recognised by an isoprenylcysteine-carboxymethyl transferase (ICMT), which fixes a methyl group thereto by esterification.

Only the maturation of the prelamin A continues with a second endoproteolytic cleaving by Face1, which releases a farnesyl-peptide of 15 amino acids and a mature lamin A. This lamin A, which no longer includes the fatty acid, becomes soluble, and is imported into the nuclear by virtue of its nuclear location signal, and is located in the nuclear lamina itself as well in the rest of the nucleus compartment, constituting a veritable nuclear skeleton (Gruenbaum et al 2005). The on the other hand mature B lamin still has at the C-terminal end its farnesylated and methylesterified cysteine. It therefore remains inserted in the envelope membrane of the reticulum, and then in the nucleoplasmic face of the nuclear envelope, and has its location exclusive to the nuclear lamina, and the internal membrane of the nuclear envelope where it is anchored.

The term prenylation should be taken to mean the fixing to the thiol group of a cysteine either of a farnesyl chain of 15 carbon atoms, and farnesylation is then spoken of, or a geranylgeranyl chain of 20 carbon atoms, and geranylgeranylation is then spoken of (Reid et al 2004), or of any other derivative of isoprene.

The farnesylation, catalysed by the farnesyl-transferase (FTase), which recognises the C-terminal consensus sequence (CaaX), preferentially fixes a farnesyl group to the cysteine residue of the unit.

Gernaylgeranylation is the fixing by geranylgeranyl-transferase (GGTase) of a geranylgeranyl group to the cysteine residue of the unit.

These fatty acids result from the biosynthesis method which, using hydroxymethyl-glutaryl-Coenzyme A, is used by the cells for manufacturing in particular cholesterol, steroids, the haem of haemoglobin and ubiquinones (Hampton et al 1996).

The family of prenylated proteins comprises approximately 300 members in the human genome, the majority of which can be identified by the C-terminal unit CaaX (Reid et al 2004). The proteins of the families Ras, Rho, Rab (Leung et al 2006), certain proteins fulfilling an import function to the mitochondria (HDJ2), some centromeric proteins (CENPE, CENPF) are in particular prenylated (Winter-Vann & Casey 2005). In general, if in the CaaX unit, X is a serine, a methionine, a cysteine, an alanine or a glutamate, the preferentially grafted isoprenoid is farnesyl. If X is a leucine, the CaaL unit will preferably recognised by the GGTase, which will catalyse the transfer of a geranylgeranyl group (Basso et al 2006). It is probable that other groups derived from isoprene can also be fixed to this cysteine, although this is not described in the literature.

In humans, there exist three lamin genes. The LNMA gene, situated at 1q21.2-q21.3 (Wydner et al 1996), gives the lamins A and C by alternating splicing. The LMNA gene is composed of 12 exons. The start of exon 1 codes the N-terminal globular end common to lamins A and C; the end of exon 1 and up to the start of exon 7 code the central helical part; finally, the other exons code the C-terminal globular end (Levy & Cau 2003).

In fact, the gene codes for 4 differently spliced products, the C lamins and the prelamin A of which are the two main ones (Lin & Worman 1993). The differential production of lamins A and C is done by the use of an alternative splicing site at exon 10 of the pre-messenger, so that the lamin C is coded by exons from 1 to 10 and the lamin A is coded by exons from 1 to 9, the first 90 pairs of bases of exon 10, and exons 11 and 12 (A-specific lamin).

Consequently the prelamin A and the lamin C peptides are identical at the first 566 amino acids, the C-terminal ends of the C lamins and the prelamin A next containing respectively 6 and 98 specific amino acids.

The type-B lamins comprise three different proteins (Shelton et al 1981): lamins B1, B2 (the two most represented isoforms) and B3. The LMNB1 gene is situated at 5q23.3-q31.1 and comprises 11 exons coding the lamin B1 (Lin & Worman 1995). The LMNB2 gene is located at 19p13.3 and codes for the lamins B2 and B3 by an alternating splicing mechanism (Biamonti et al 1992).

The type-B lamins are expressed constitutively in all the cells as from the first development stages, while the type A lamins are in general absent in the embryonic strain cells (Rober et al 1989, Stewart et al 1987) and are expressed in all the differentiated somatic cells. Their expression is subject to regulations according to the tissue and during life (Duque et al 2006). It seems that their expression is not necessary, since mice in which the lamin A expression has been specifically blocked, but which all the same express the lamin C and the other lamins, do not have any apparent phenotype (Fong et al 2006).

The lamins interact with a very high number of protein partners having very diverse functions; they are consequently involved in a large number of nuclear processes, including DNA replication and repair, control of transcription and splicing, organisation of the chromatin structure (for journal, see Shumaker et al 2003, Zastrow et al 2004, Hutchison et al 2004, Gruenbaum et al 2005). Alterations to the structure of the lamina give rise to numerous human hereditary pathologies. They are due to mutations of the genes coding the lamins, or other proteins of the lamina. These pathologies have been grouped together under the generic term laminopathies (Broers et al 2006, Mattout et al 2006). Recently, mutations in the genes of the enzymes responsible for the maturation of lamins (Facet in particular) have been identified, giving rise to pathologies also belonging to the group of laminopathies (Navarro et al 2004 and 2005).

At the present time, the only pathology in humans associated with mutations of the LMNB1 or 2 genes is a leucodystrophy caused by a complete duplication of the LMNB1 gene (Padiath et al 2006). A doubt remains on the potential implication of variation sequences found in LMNB2 in patients suffering from Barraquer-Simon syndrome (Hegele et al 2006). However, it has been demonstrated in vitro by RNAi (RNA-interference) experiments (Harborth et al 2001), and in the murin model (Vergnes et al 2004), that type B lamins are essential for cell development and integrity. This is because a lamin B1 deficiency causes perinatal mortality in mice. Moreover, the nuclei of the embryonic fibroblasts of the same LMNB1 deficient mice show remarkable alterations in the nucleus morphology, close to those observed in patients carrying mutations of the LMNA gene. In addition, it has been shown recently that B-type lamins are necessary to the formation of the division spindle during mitosis, which tends to prove that their role is dynamic and multiple during the cell cycle, not only restricted to maintenance of the architecture of the nucleus (Tsai et al 2006). On this latter role, a recent article demonstrates the structural function of the B-type lamins: cells artificially deprived of B1-type lamins have a "floating" nucleus in the cell, which turns on itself (Li et al 2007). The functional redundancy existing between the two lamins B1 and B2 is no doubt also a direct reflection of their indispensability, exerting a high selection pressure and masking the effect of any mutations of the sequence of corresponding genes.

The functional alterations in the A/C lamins, due to mutations of the LMNA gene, give rise to at least 15 disorders including very diverse pathologies in a clinical spectrum ranging from mild forms, affecting a tissue in an isolated fashion, to systemic forms that are fatal in the perinatal period.

Many mutations of the LMNA gene appreciably modify the assembly of proteins in the nuclear envelope and disturb their functioning. In the cells of various tissues, the morphology of the nuclei is altered: they often have hernias that extrude genetic material in the cytoplasm (Goldman et al 2004).

The proteins normally associated with the nuclear envelope, the B lamins, certain proteins of the nuclear pores and the LAP2 proteins are absent from the periphery of these hernias.

These morphological anomalies are followed by functional alterations, which end up by causing cell deaths. Among all the pathologies grouped together under the term laminopathies, only those relating to the abnormal accumulation of a prenylated form of protein relate to the present invention.

These are mainly the Hutchinson-Gilford syndrome, or Progeria (De Sandre-Giovannoli et at 2003, Eriksson et al 2003), and restricted dermopathy (Navarro et al 2004). In these 2 syndromes, the physiopathological cause is an accumulation and persistence in the cells of the patients of non-matured farnesylated prelamin A.

Restrictive dermopathy, fatal around the natal period, is characterised by clinical signs that are almost all the consequence of a cutaneous deficit that restricts movements in utero. This pathology is very rare. The skin is rigid and tensioned, and yields in places, causing for example tears at the armpits or neck. The eyelashes, eyebrows and skin hair are absent or very sparse. Hydramnios is often present, and a reduction in fetal movements is signaled as from the sixth month of pregnancy. At the skeletal level, radiography reveals contractions at all of the joints, deformed feet, thin, dysplastic and bi-partited clavicles, ribbon-shaped ribs, tubular long bones of the arms and demineralisation at the cranium. Transmission of fatal restrictive dermopathy is autosomal recessive.

LMNA and ZMPSTE24/Face1 mutations have been reported for this pathology (Navarro et al 2004). In both cases, the physiopathological mechanism is the same: the prelamin A cannot mature (zero Face1 mutation or disappearance of the cleavage site by mutation of the prelamin A), and remains farnesylated, and therefore inserted in the nuclear membrane. The accumulation and persistence in the cells of these abnormal precursors, which probably prevent normal interaction of the lamins B and C with their partners, causes death of the cells and, very soon, of the patient. It has been clearly demonstrated that it is indeed the persistence of the farnesylated group rather than the absence of mature lamin A, as might have been thought at first, that is responsible for the cell toxicity (Fong et al 2004).

In April 2003, from cross-checking the symptoms common to acromandibular dysplasia and some diseases resulting in premature aging, the inventors showed that Progeria, the most typical and most serious form of premature aging, results from a mutation of the LMNA gene (De Sandre-Giovannoli et al 2003). Children afflicted by this illness, also referred to as Hutchinson-Gilford syndrome, suffer from accelerated aging, up to ten times more rapid than that of a normal individual, and have a life expectancy that does not exceed 13 years. In France, one child out of approximately six million is affected. The symptoms are cutaneous aging, baldness, reduction in the size of the jaw and problems related to old age, for example stiffness in the joints and cardiovascular disorders. The latter, such as myocardial infarction or atherosclerosis, are often the cause of death.

The mutation involved, situated at exon 11 of the LMNA gene, activates a cryptic splicing site of the pre-mRNA, leading to a deleted mRNA of 150 nucleotides (De Sandre-Giovannoli et at 2003, Eriksson et al 2003). This deleted mRNA is translated into an abnormal prelamin A, progerin, which cannot be matured into normal lamin A: the absence of 50 amino acids of exon 11 comprising the protease recognition site blocks the second cleavage of the progerin, the C-terminal end of which keeps its farnesylated group. It therefore remains inserted in the nucleoplasmic face of the nuclear envelope, which has characteristic alterations, hernias of the nucleoplasm in the cytosol and abnormalities in the distribution of the peripheral heterochromatin (Goldman et al 2004). Here also, it is the persistence of the farnesylated group, moreover necessary for anchoring to the envelope membrane of the reticulum in which there are located some of the enzymes responsible for maturation (cleavages, methylation) which is responsible for the cell toxicity of the progerin (Fong et al 2004).

These systemic pathologies have the particularity of being associated with the premature appearance of signs normally related to aging. Their common physiopathological characteristic is to generate a prenylated lamin, with the consequences described.

Two recent studies have shown that a reduction in the intranuclear accumulation of the farnesylated prelamin, truncated or not, effectively prevents the appearance of the cell phenotype. The first was carried out on the progeroid murin model deficient in Face1 protease (Pendas et al 2002). When they are crossed with mice expressing half the amount of lamin A (LMNA+/−mouse), the effects of the absence of Face1 are less (Varela et al 2005). The second study shows that the treatment of cells of HGPS patients with morpholino (antisens oligonucleotides) targeting the cryptic splicing site does away with the mutant phenotype (Scaffidi & Misteli 2005).

Several recent studies (Scaffidi & Misteli 2006, Cao et al 2007) show the involvement of lamin A in the physiological aging process. In particular, it has been demonstrated that, during physiological aging, an aberrant lamin A accumulates over time at the periphery of the cell nucleus. This aberrant lamin is fact progerin, the cell, during its normal life and functioning accidently using from time to time the cryptic splicing site of exon 11, the progerin produced accumulates little by little under the lamina. Finally, the "normal" aged cell may present hernias characteristic of a laminopathy caused by these accidental splicing events, which cause its death.

It appears that identical molecular mechanisms are firstly responsible for the signs of premature aging in individuals suffering from Progeria and secondly, at a much lower level, are involved in the physiological aging of individuals not carrying mutations.

There exist in the prior art two therapeutic approaches described for improving the cell phenotype caused by the pathological production of progerin. The first of these solutions is quite simply to prevent the use by the spliceosome of this cryptic splicing site in exon 11, by "masking" it by treatment with an antisens oligonucleotide (Scaffidi & Mistelli 2005), or with a retrovirus producing an siRNA (Huang et al 2005). The results are promising in vitro, but it is a case here of "gene" therapy, and the development of a medication around this approach is necessarily long and complicated, with all the drawbacks related to the vectorisation of the OASs in order to obtain an in vivo effect. The second solution consists of inhibiting the farnesyl-transferase, the enzyme that catalyses the transfer of the farnesyl group on the prelamins from farnesyl-pyrophosphate. When such inhibitors (FTI) are used, a "normal" nuclear envelope is only partially restored on HGPS cells (Progeria) in culture, and the survival of RD mice (KO ZMPSTE24) is improved (Glynn & Glover 2005, Capell et al 2005, Toth et at 2005, Fong et al 2006).

However, blocking and farnesylation may cause a compensatory geranylgeranylation (Bishop et al 2003).

In addition, it has been reported recently that FTIs cause a stoppage of the cell cycle by blocking the proteasome (Demyanets et al 2006, Efuet & Keyomarsi 2006). Thus the treatment no doubt causes an accumulation in the nucleoplasm of progerin probably ubiquitinylated not degraded by the proteasome.

In addition, recent works report that the reduction in the level of farnesylation of the progerin in vivo is very low, around 5% (Young et al 2006), which does not suffice to explain the restoration in the nuclear morphology observed in vitro.

Finally, the FTIs are specific to only one of the protein prenylation routes and cannot be envisaged as global inhibitors of post-translation prenylations.

Moreover, it is reported that the total absence of one of the enzymes of this route, mevalonate-kinase, is fatal during infancy (homozygote mutation loss of function of the gene coding for this enzyme, a syndrome reported by Hoffmann et al 2003).

BRIEF SUMMARY OF THE INVENTION

After lengthy research, the inventors have shown that the association of an inhibitor of hydroxymethylglutaryl-coenzyme A reductase (the statin family) and an inhibitor of farnesyl-pyrophosphate synthase (amino-bisphosphonates family, NBP), or of one of their physiologically acceptable salts, is an effective treatment for conditions, pathological or otherwise, related to the accumulation and/or persistence in cells of prenylated proteins, in that it blocks all the protein prenylation channel, both C15 and C20, or in the non-characterised forms. The inventors have also found that the association of an inhibitor of hydroxymethylglutaryl-coenzyme A (HMG-CoA) reductase and an inhibitor of farnesyl-pyrophosphate synthase has a synergetic effect of the restoration of the normal phenotype in fibroblasts of patients affected with Progeria. The effect of the association is appreciably greater than the effect of one or other of the inhibitors used individually.

The use of the association on cells of patients suffering from Progeria leads to an inhibition of the prenylation of proteins, and therefore to the appearance of non-farnesylated prelamin A and the improvement of nuclear symptoms.

DETAILED DESCRIPTION OF THE INVENTION

The results make it possible to envisage the use of an inhibitor of hydroxymethylglutaryl-coenzyme A (HMG-CoA) reductase and an inhibitor of farnesyl-pyrophosphate synthase, or one of their physiologically acceptable salts, in the preparation of a composition, in particular of a pharmaceutical composition, intended for the treatment of conditions, pathological or otherwise, related to the accumulation and/or persistence of prenylated proteins in cells.

Thus an object of the invention is the use of at least one inhibitor of hydroxymethylglutaryl-coenzyme A (HMG-CoA) reductase and at least one inhibitor of farnesyl-pyrophosphate synthase, or one of their physiologically acceptable salts, in the preparation of a composition, in particular a pharmaceutical composition, intended for the treatment of conditions, pathological or otherwise, related to the accumulation and/or persistence of prenylated proteins in cells.

It is also within the scope of the invention to use compounds that are both inhibitors of hydroxymethylglutaryl-coenzyme A (HMG-CoA) reductase and inhibitors of farnesyl-pyrophosphate synthase.

Advantageously, the composition according to the invention can be intended for the treatment of conditions, pathological or otherwise, related to the accumulation and/or persistence in cells of farnesylated and/or geranylgeranylated proteins.

Very particularly, the composition according to the invention can be intended for the treatment of conditions, pathological or otherwise, related to the accumulation and/or persistence in cells of progerin, even more particularly to the treatment of conditions related to the accumulation and/or persistence in cells of farnesylated prelamin A, whether or not this be truncated or modified.

In particular, since it is accepted that physiological aging involves the accumulation of progerin in cells during life and that progerin is concentrated in particular in the mesenchymatous cells, the composition according to the invention can be intended to prevent the effects of cell aging, in particular with regard to the skin and/or the vascular endothelium.

The composition according to the invention can be intended for the treatment of any living being, human or animal, particularly for the prevention of the effects of cell aging. The composition therefore finds an application both in human medicine and in veterinary medicine.

According to the invention, any inhibitor of farnesyl-pyrophosphate synthase or one of its physiologically acceptable salts can be used in the preparation of the composition according to the invention.

The physiologically acceptable salts may for example be salts formed with hydrochloric, bromhydric, nitric, sulphuric or phosphoric acids, carboxylic acids such as for example acetic, formic, propionic, benzoic, maleic, fumaric, succinic, tartric, citric, oxalic, glyoxylic or aspartic acids, alkane sulphonic such as methane or ethane sulphonic acids, or arylsulphonic such as benzene or para-toluene sulphonic acids.

Particularly inhibitive of farnesyl-pyrophosphate synthase may be one of the members of polyphosphonate family, particularly aminobisphosphonates (NBPs), or one of its physiological acceptable salts.

Polyphosphonates are synthetic molecules very much used in the treatment of osteoporosis and bone regeneration.

The term phosphonate applies to molecules very similar to phosphate:

Phosphonate     Phosphate

The core of the bisphosphonates (BPs) is equivalent to a P—O—P bond as in ATP for example, but where the oxygen is replaced by a carbon. This confers special stability on these molecules.

A simple bisphosphonate with the equivalent ADP, the two phosphate groups ($O_3P$—) being replaced by the bisphosphonate group.

The central carbon, unlike oxygen in phosphates, may also be involved in two bonds, and it is the nature of the groups grafted onto this carbon that makes the specificity of bisphosphonates.

When the "lateral" chains (R1 and R2) comprise an amine function (NH), or more generally one or more nitrogen atoms, amino bisphosphonate, or NBP, is spoken of.

Naturally other substituents can be fixed to the oxygens.

Pyrophosphoric acid, or pyrophosphonate in solution (PPi)

Pyrophosphoric acid is used in many metabolic reactions as a substrate transporter, and is restored at the end of the reaction. One of the metabolic routes using molecules coupled to pyrophosphate is that of protein prenylation.

The grafting of isopentenyl-PP (C5 base unit) onto a geranyl-PP (C10) in order to give farnesyl-PP, a reaction catalysed by the enzyme farnesyl-pyrophosphate synthase (FPS), releases a PPi.

It is this step that is specifically inhibited by the NBPs.

In this regard and by way of example, the aminobisphosphonate (farnesyl-pyrophosphate synthase inhibitor) can be chosen from alendronic acid or its ionic form, alendronate;
clodronic acid or its ionic form, clodronate;
etidronic acid or its ionic form, etidronate;
ibandronic acid or its ionic form, ibandronate;
medronic acid or its ionic form, medronate;
neridronic acid or its ionic form, neridronate;
olpadronic acid or its ionic form, olpadronate;
pamidronic acid or its ionic form, pamidronate;
risedronic acid or its ionic form, risedronate;
tiludronic acid or its ionic form, tiludronate;
zoledronic acid or its ionic form, zoledronate;
4-N,N-dimethylaminomethane diphosphonic acid or its ionic form, dimethylaminomethanediphosphonate;
α-amino-(4-hydroxybenzylidene)diphosphonate.

Preferentially according to the invention, it is preferred to use zoledronic acid (also called zolendronic acid) or its ionic form, zoledronate (also called zolendronate).

According to the invention, any inhibitor of HMG-CoA reductase, or one of its physiological acceptable salts, can be used in the preparation of the composition.

In particular the inhibitor of HMG-CoA reductase can be a molecule in the family of statins, whether it be liposoluble or hydrosoluble, or one of its physiologically acceptable sales.

Statins have been revealed in mushrooms. They have an inhibiting activity for HMG-CoA reductase, a key enzyme in the biosynthesis of cholesterol and steroids, which catalyses the reduction of the hydroxymethylglutarate coupled to the coenzyme A in mevalonic acid (mevalonate in solution). This inhibition is provided by their structural analogy with the skeleton of hydroxymethylglutarate. The metabolic route involved is certainly that of the biosynthesis of cholesterol, but it is also that of the synthesis of the prenyl groups, polymers of the base unit with 5 isoprene carbons used for modifying approximately 300 proteins in the cells and attaching to them a lypophilic tail, allowing in particular their anchoring in the membranes.

The main polyprenes, all issuing from pyruvate and HMG-CoA, are geranyl (C10), farnesyl (C15) and geranylgeranyl (C20).

All the statins are hepatoselective overall, but not all have the same mode of entry into the cells. This is because pravastatin and rosuvastatin are both hydrophilic, and therefore hydrosoluble, unlike all the others, which are lipophylic, and therefore can diffuse freely through the membranes (lipid bilayers), which no doubt explains their greater toxicity. Hydrosoluble statins need a specific transporter for entering the cell, Organic Anion Transport 3, or OAT3, or SLC22A8 (Takedaa et al 2004).

They are very much used for the treatment of hypercholesterolaemia, and their secondary effects, which are rare, are well characterised. These are in particular cases of rhabdomyolysis (1% to 7% of cases according to the molecule used, Evans et al 2002), the precursory sign of which, muscular pain in the patient being treated, gives rise to the immediate stoppage of the treatment.

In this regard and by way of example, a statin can be chosen from atorvastatin, simvastatin, pravastatin, rivastatin, mevastatin (or compactin), fluindostatin, velostatin, fluvastatin, dalvastatin, cerivastatin, pentostatin, rosuvastatin, lovastatin, pitavastatin, or one of their physiologically acceptable salts.

Lovastatin, pravastatin and simvastatin are molecules derived from fungal metabolites, while the others (atorvastatin, cerivastatin, fluvastatin, pitavastatin and rosuvastatin) are entirely synthetic. Preferentially, according to the invention, privastatin is used, a hydrosoluble semi-natural statin.

Naturally it is possible according to the invention to use one or even two or more inhibitors of farnesyl-pyrophosphate synthase associated with one or even two or more inhibitors of HMG-CoA reductase.

According to a particular form of the invention, the composition can be intended for the treatment of conditions, pathological or otherwise, requiring inhibiting the prenylation of proteins. These pathologies may be labelled or not, for example Costello or Noonan syndrome, cardio-fascio-cutaneous syndrome, or illnesses related to an abnormal or persistent prenylation of Ras and signal transduction proteins.

According to yet another particular form of the invention, the composition can be intended for the treatment of conditions, pathological or not, presenting signs of aging, whether it be natural, premature or accelerated. In particular in the case of signs of deterioration of the vascular endothelium (protection of the vascular endothelium), aging of the skin, and bone lysis.

Preferentially, the composition according to the invention is a pharmaceutical composition intended for the treatment of Progeria (HGPS, Hutchinson-Gilford Progeria Syndrome) and restrictive dermopathy (RD).

According to the invention, the inhibitor of farnesyl-pyrophosphate synthase and the inhibitor of HMG-CoA reductase are advantageously present in the composition at physiologically effective doses.

In general terms, the doses to be administered can be adapted by persons skilled in the art according to the patient, the pathology, the administration mode, etc. Naturally, repeated administrations may be performed, possibly in combination with other active ingredients or any vehicle acceptable on a physiological level (buffers, saline solutions, isotonic solutions, with stabilisers, etc).

In general the daily dose of the inhibitors will be the minimum dose for obtaining the required therapeutic effect.

Compositions using an inhibitor of hydroxymethylglutaryl-coenzyme A (HMG-CoA) reductase and an inhibitor of farnesyl-pyrophosphate synthase according to the invention can be formulated for the digestive or parenteral route.

The said compositions can also comprise at least one other active ingredient, in particular another therapeutically active ingredient, for simultaneous or separate use or use staged over time.

According to the invention, the inhibitor hydroxymethylglutaryl-coenzyme A (HMG-CoA) reductase and the inhibitor of farnesyl-pyrophosphate synthase can be used in the composition, in a mixture with one or more excipients or in inert vehicles, that is to say physiologically inactive and non-toxic. Saline, physiological, isotonic, buffered, etc solutions compatible with physiological usage and known to persons skilled in the art can for example be cited.

The compositions may contain one or more agents or vehicles chosen from dispersants, solubilising agents, stabilisers, preservatives, etc. Agents or vehicles that can be used in formulations (liquid and/or injectable and/or solid) are in particular methyl cellulose, hydroxymethyl cellulose, carboxymethyl cellulose, cyclodextrins, polysorbate 80, mannitol, gelatine, lactose, vegetable or animal oils, acacia, etc.

The compositions can be formulated in the form of injectable suspension, gels, oils, tablets, suppositories, powders, capsules, etc, possibly by means of galenic forms or devices providing prolonged and/or delayed release. For this type of formulation, an agent such as cellulose, carbonates or starches is advantageously used.

Administration can be achieved by any method known to persons skilled in the art, preferably by oral route or injection, typically by intramuscular, intravenous or intra-peritoneal route, Administration by oral route is preferred.

When it is a case of long-term treatment, the preferred administration method will be sublingual, oral or transcutaneous.

BRIEF DESCRIPTION OF THE DRAWINGS

5a: photograph representing mice aged 3 months and respectively wild, Zmpste24$^{-/-}$ and Zmpste24$^{-/-}$ treated.

5b: weight of the wild mice (n=6), Zmpste24$^{-/-}$ non-treated (n=7) and treated (n=8), at 3 months.

5c: survival curve (type Kaplan-Meier) showing the significant extension of the survival of treated females (n=7) (-◇-) in comparison with non-treated mice (n=7) (-ʋ-).

5d: tomography image, reconstituted in 3D, by μCT scanner of tibias of mice treated and not treated (at the top). At the bottom, representation of the bone volume (on the left, a) and the number of trabeculae per square millimeter (on the right, b).

5e: quantification of nuclear abnormalities (%) on liver cells. On the left, fluorescent marking of the nuclei with DAPI, on the right, counting of the number of abnormal nuclei.

EXAMPLES

The following examples serve to illustrate the invention without in any way limiting it.

Example 1

Synergetic Synergistic Effect of the Association of an Inhibitor of Water-Soluble Hydroxymethylglutaryl-Coenzyme A (HMG-CoA) Reductase and an Inhibitor of Farnesyl-Pyrophosphate Synthase on Cultures of Normal Cells and Progeroids A) Protocols Cells and Cell Culture The cell lines are either reference fibroblasts AG16409 from the Coriell Institute, or fibroblasts from biopsies of patients suffering from Restrictive Dermopathy. They are cultivated at 37° C. in 5% $CO_2$ in a P2 room.

The normal complete culture medium is
RPMI (Invitrogen) supplemented with
Fetal calf serum 20% (Invitrogen)
L-Glutamine 200 mM (Invitrogen)
Penicillin/Streptomycin/Fungizone 1× mixture (Stock 100×, Cambrex)

Harvesting of Cells

The cells are harvested by trypsinisation in the following manner (protocol for a large flask, 75 cm$^2$, BD Falcon):

The medium is aspirated;

The cells are washed with 10 ml of PBS 1× (Invitrogen), 10 ml;

5 ml of a solution of trypsin/EDTA 1× (Cambrex) is added

The flask is incubated for a period of approximately 6 minutes at 37° C., the time during which the cells detach;

The trypsin is inhibited by dilution in 15 ml of complete medium;

The cells are concentrated by centrifugation for 10 minutes at 1000 revolutions per minute at 16° C.;

The concentrate is re-suspended in 2 ml of PBS 1×, and re-centrifuged under the same conditions;

Either the cells are frozen for subsequent use or are transplanted from this washed concentrate.

Treatments

The pravastatin solution (water-soluble statin) used is prepared as follows:

40 mg of pravastatin (Sigma Aldrich, P4498) is taken up in sterile water in order to form a stock solution at 10 mM.

The final concentrations tested were 500 nM, 1, 5, 50 and 100 μM, obtained by diluting the stock solution in complete medium.

The solution of zoledronate (NBP) used is prepared as follows:

A stock solution of (1-hydroxy-2-imidazol-1-yl-phosphono-ethyl) phosphonic acid (0.8 mg/ml, Novartis) is adjusted to a concentration of 2 mM.

The final concentrations tested were 500 mM, 1, 5, 50 and 100 μM, obtained by diluting the stock solution in complete medium.

Western Blot

Preparation of Cells

For a Western blot experiment, the cells are treated as follows:

Approximately 7.5×10$^5$ cells are seeded in a large flask and cultivated under the following conditions until there is almost confluence (4 days).

At the end of 4 days, the cells are washed with PBS 1X and taken up in the complete medium supplemented with the treatment.

The cells are incubated for the processing time (from 6 to 72 hours, sequentially or simultaneously) in the incubator at 37° C.

At the end of the processing, the cells are trypsinised (above protocol) and the concentrate obtained is stored at −80° C. until the proteins are extracted.

Extraction of the Proteins for Western Blot

The cell concentrate is taken up in 300 μl of lysis buffer

| | |
|---|---|
| Triton X100 | 1% |
| SDS | 0.1% |
| Sodium deoxycholate | 0.5% |
| NaCl | 50 mM |
| EDTA | 1 mM |
| TrisHCl pH 7.4 | 20 mM |
| Protease inhibitor (Roche 11697498001) | 1 pellet per 50 ml |
| Extemporaneously, there are added | |
| Sodium orthovanadate | 1 mM |
| PMSF | 1 mM |

The cells are exposed to sonication for twice 30 seconds (Brandson Sonifier Cell Disruptor B15)

The cell debris is centrifuged for 10 minutes as 10,000 revolutions per minute at 4° C.

The protein supernatant is stored at −80° C. until use.

The dosing of the proteins is carried out on defrosting.

Western Blot

Gel

An 8% acrylamide gel is conventionally used for detecting the different forms of A/C-type lamins.

| | |
|---|---|
| Acrylamide/bisacrylamide 37/1 | 8% |
| TrisHCl pH 8.8 | 375 mM |
| SDS | 0.1% |
| APS | 0.1% |
| TEMED | 0.01% |

A concentration gel is poured onto the separative gel

| Acrylamide/bisacrylamide 37.5/1 | 3% |
|---|---|
| TrisHCl pH 8.8 | 375 mM |
| SDS | 0.1% |
| APS | 0.1% |
| TEMED | 0.01% |

The protein concentration of the samples is analysed, and aliquots are adjusted to 50 μg per tube in lysis buffer to qsp 15 μl.

5 μl of charge buffer is added to each sample.

| SDS | 4% |
|---|---|
| TrisHCl pH 6.8 | 100 mM |
| Glycerol | 20% |
| β-mercaptoethanol | 20% |
| Bromophenol blue | traces |

The samples are denatured by heating for 5 minutes at 95° C. and deposited in the wells.

Migration takes place at 50 and then 100 volts, in a buffer

| Tris-base | 0.3% |
|---|---|
| Glycine | 1.44% |
| SDS | 0.1% |

Transfer

The transfer membrane (Hybon P, Amersham Biosciences) is prepared by soaking in ethanol, followed by a bath for 5 minutes in sterile water, and 10 minutes in the transfer buffer:

| Tris-base | 12 mM |
|---|---|
| Glycine | 96 mM |
| Ethanol | 20% |

The gel is moistened for 20 minutes in the transfer buffer and then the sandwich is mounted (Miniprotean system, Biorad).

The transfer takes place in general overnight, in a cold chamber, at 10 volts.

The membrane is rinsed in PBS 1×, stored away from moisture, and used as it is for detection.

Detection

The membrane is incubated for 1 hour at room temperature in a saturation solution:

| Casein | 10% |
|---|---|
| Tween 20 | 0.1% |
| PBS | 1X |

It is rinsed for twice 10 minutes in a washing buffer (Tween 20 0.1%/PBS 1×).

The primary antibody is diluted in the saturation buffer (details and dilution, see below immunomarking).

The membrane is incubated with the primary antibodies for 1 hour at room temperature under stirring.

At the end, it is rinsed 3 times with washing buffer and then washed for 3 times 15 minutes with the same buffer.

The secondary antibody (system coupled to peroxydase, Jackson Immunoresearch) is diluted to $1/10000^{th}$ in saturation buffer.

The membrane is incubated with this solution for 30 to 45 minutes at room temperature under stirring.

At the end, it is rinsed 3 times with washing buffer and then washed for 3 times 15 minutes with the same buffer.

Detection is carried out with the ECL Plus Western Blotting System kit from Amersham Bioscience, according to the indications of the supplier.

After revelation, the membrane is exposed on Biomax MR film (Kodak), for the time necessary to have a satisfactory signal.

Immunomarking

Preparation of Cells

A cell culture is trypsinised and the cells counted on a Neubauer cell.

Labtech-style culture wells (Nunc, ref 177399) are seeded, at the rate of $5\times10^4$ cells per well.

The complete culture medium is supplemented by the treatment or treatments (statin, NBP, or both), and the cells cultivated for an ad hoc time.

At the end, the culture medium is aspirated and the wells dismantled.

The plates are washed in PBS 1×.

The cells are fixed in a paraformaldehyde 4% solution (in PBS) for 10 minutes at room temperature.

Washing for 10 minutes in PBS 1× is carried out.

The cells are dehydrated by successive baths of 3 minutes in solutions with an increasing ethanol percentage (70%, 90%, 100%, the latter bath being repeated).

After drying, the plates are stored at −80° C. until use.

Marking

After defrosting, the cells are incubated for 5 minutes at room temperature in a humid chamber in 50 μl of a permeabilisation solution:

| PBS | 1X |
|---|---|
| Triton X100 | 0.5% |
| RNS (Rabbit Normal Serum, Vector S5000) | 5% |
| Protease inhibitor (Roche 11697498001) | 1 pellet per 50 ml |

3 pre-incubation baths each of 15 minutes are effected in 50 μl of the incubation solution:

| PBS | 1X |
|---|---|
| RNS | 5% |
| Protease inhibitor (Roche 11697498001) | 1 pellet per 50 ml |

The primary antibody is diluted to $1/100^{th}$ in 50 μl of incubation solution and put in contact with the cells for 1 hour at room temperature in a humid chamber.

The primary antibodies used are of 2 types:

Anti-lamin mouse A/C (N-terminal side), clone 4A7, donated by G Morris (Oswestry, UK)

Goat anti-prelamin A (15 as C-terminal end), product SC6214, Santa Cruz Biotechnology Inc.

Three rinsings in 50 μl of PBS 1× are carried out each for 15 minutes.

Incubation with the secondary antibody takes place for 1 hour in 50 ml of incubation solution at room temperature in a humid chamber. The secondary antibodies are of two types:

Anti-mouse donkey, Jackson Immunoresearch, dilution to $1/100^{th}$

Anti-goat donkey, Jackson Immunoresearch, dilution to $1/200^{th}$

Three rinsings in 50 µl of PBS 1× are carried out each for 10 minutes.

An incubation with 100 µl of DAPI 50 ng/ml solution (SERVA, ref 18860) is carried for 15 minutes at room temperature in a humid chamber.

Three rinsings in PBS 1× are carried out plate-holder tanks each for 5 minutes.

A final rinsing is carried out for 5 minutes in a 0.1% solution of Tween20 in PBS.

Mounting

The cells are immersed in a drop of VectaShield (Vector), covered with an object-covering blade and observed on a fluorescence microscope (Leica DMR, Leica Microsystems), equipped with a coolSNAP (Princeton) camera system.

B) Results

Figure 1:
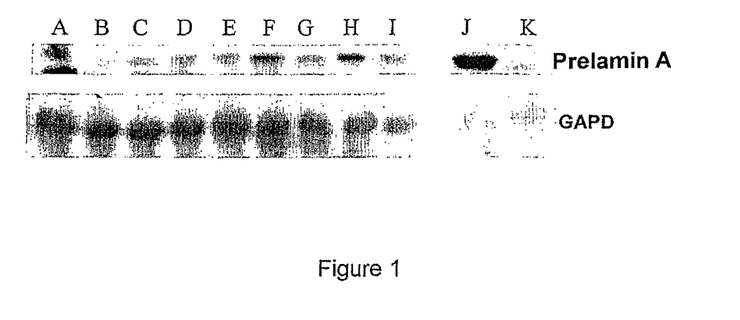
FIG. 1 illustrates the results obtained in Western Blot on "normal" reference fibroblasts treated with increasing doses of a hydrosoluble statin (pravastatin P, 20 to 100 μm), and an aminobisphosphonate (NBP zoledronate Z, 20 to 100 μm) ((Tracks A to I, respectively P20/Z20, P20/Z60, P20/Z100, P60/Z20, P60/Z60, P60/Z100, P100/Z20, P100/Z60, P100/Z100)). Track J is a positive control for the presence of prelamin A (fibroblasts of patients DR), track K is the negative control, treated with the solvent alone (PBS).

B.1) Western Blot (FIG. 1)

"Normal" reference fibroblasts were treated with a water-soluble statin (pravastatin P, 20 to 100 µM), and with an aminobisphosphonate (NBP zoledronate Z, 20 to 100 µm) in association (tracks A to I, respectively P20/Z20, P20/Z60, P20/Z100, P60/Z20, P60/Z60, P60/Z100, P100/Z20, P100/Z60, P100/Z100). The Western blot shows the "appearance" of a band corresponding to the size of the immature (non-truncated) prelamin A according to the increase in concentration of the two molecules, which confirms that farnesylation is necessary for the maturation of the lamin A. This result shows that the blocking of the synthesis of the farnesyl-PP at 2 points in the metabolic route is more effective than a blocking at a single point on the inhibition of the farnesylation of the prelamin A, at least ex vivo.

Figure 2:
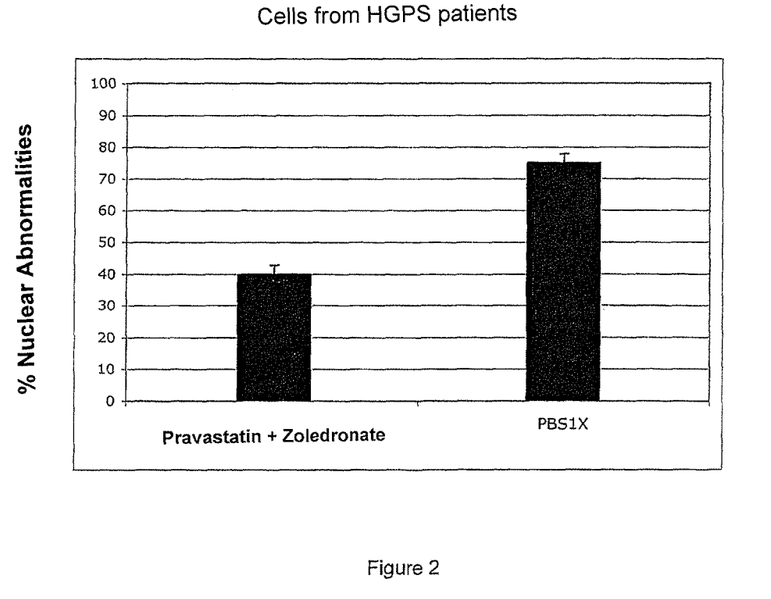
FIG. 2 illustrates the results obtained at effective doses of each of the products.

B.2) Dose and Duration Response in Immunohistochemistry (FIG. 2)

Dose-response and duration-response curves made it possible to determine a maximum efficacy by measuring 2 parameters on healthy reference cells on the one hand and then on cells of HGPS patients. The most effective combination of pravastatin (water-soluble)/zoledronate (NBP) is obtained for 1 µM of pravastatin for 24 hours and then zoledronate for 12 hours: on healthy cells, no toxicity is observed, whereas on HGPS cells (cells with nuclear abnormalities), the number of "deformed" cells drops from 75% to 40%. At the same time, the level of prelamin A obtained on healthy cells is maximum.

Figure 3:
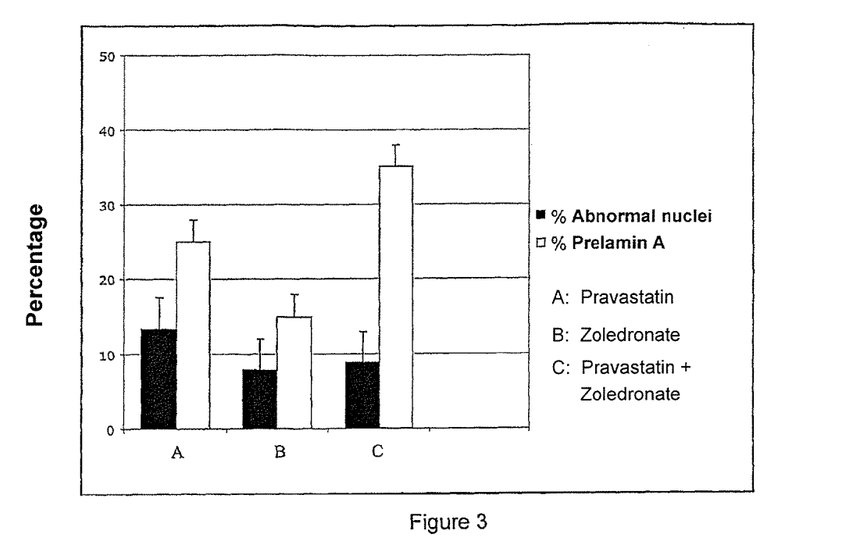
FIG. 3 illustrates the superior effect obtained when the 2 products are administered together.

B.3) Effect of the Immunohistochemistry Treatment (FIG. 3)

The combined action of the pravastatin and zoledronate shows better efficacy since the level of prelamin A produced in treated healthy cells (estimated at 35%) is much higher in combination than if the molecules are added alone (respectively 25% and 15%). On the other hand, the level of deformed nuclei (the sign of toxicity on the healthy cells) is minimal (below 10%), less than it is on cells treated with pravastatin alone for example (approximately 12%).

Treatment: Pravastatin 100 µM for 12 hours, zoledronate 20 µM for 6 hours.

Figure 4:
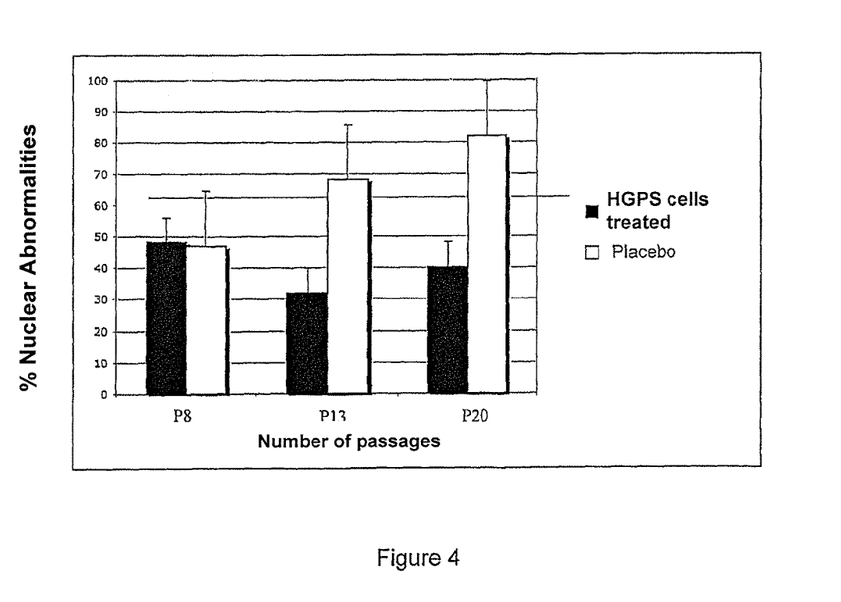
FIG. 4 illustrates the action of the association of the 2 products on aged cells.

B.4) Action on Aged Cells in Immunohistochemistry (FIG. 4)

According to the number of "passes" (the number of cell re-injections), and therefore the age of the cells, the proportion of abnormal nuclei increases, which is a characteristic of the untreated HGPS cells. If they are treated, this proportion is maintained, and even decreases a little (less than 40% as against more than 80% in the cells treated with a placebo). Treatment: Pravastatin 1 µM for 24 hours, Zoledronate 1 µM for 12 hours.

B.5) Conclusion

The pravastatin/zoledronate combination is effective at doses for which almost no effect is observed with the molecules administered separately.

The physiological effect of the blocking of the prenylation channel is therefore obtained with doses much lower than those used in single treatment in articles published on cell cultures (Kusuyama et al 2006, 10 µM of pravastatin alone on progenitors of vascular cells; Flint et al 1997, 25 µM of pravastatin alone on neonatal rat muscle cells).

Example 2

Figure 5:
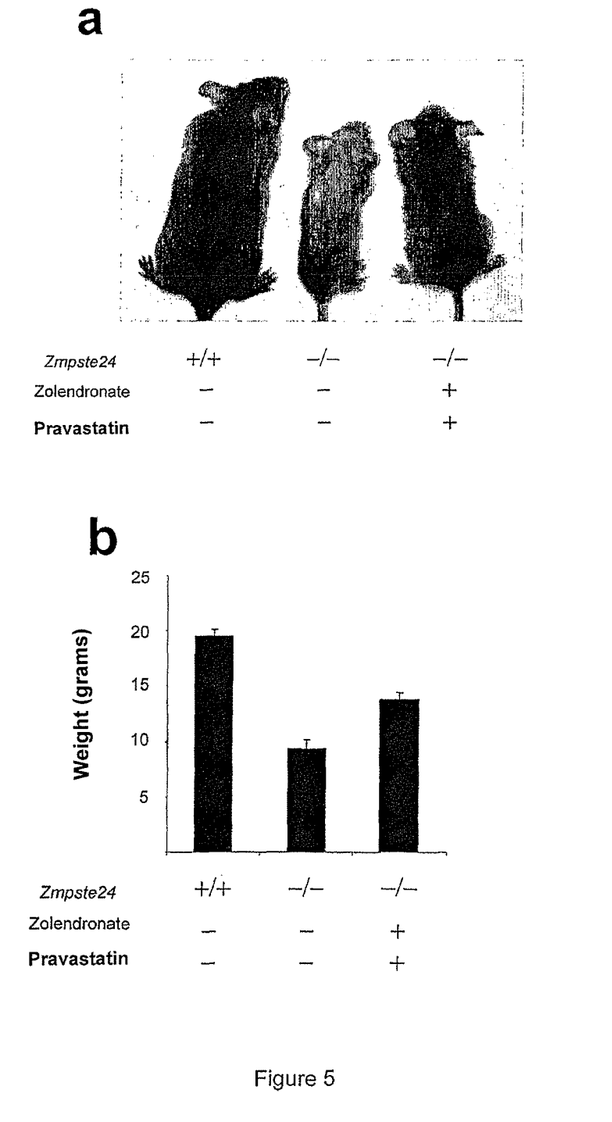
FIG. 5 illustrates the action of the association of the 2 products on model mice of Progeria (not synthesising the Face1 enzyme).

Effect of the Combination of an Inhibitor of Water-Soluble Hydroxymethylglutaryl-Coenzyme A (HMG-CoA) Reductase and an Inhibitor of Farnesyl-Pyrophosphate Synthase on a Mouse Model Having a Progeroid Syndrome (FIG. 5)

The KO Zmpste24$^{-/-}$ mice used here are those described in the article cited by Varela et al 2005. They are raised in a breeding farm in a controlled atmosphere, in a 12 hour day/12 hour night cycle, at a temperature of 20±2° C. and humidity of 50% and with access when desired to food and water. The 2 molecules (Zometa 100 µg/kg/day and Pravastatin 100 µg/kg/day) are dissolved in PBS 1× and injected by intraperitoneal route, daily, on mice aged from 1 month until their death. The controls are wild mice of the same type, treated with PBS 1× alone. The weight is measured daily, and the survival of the mice is set out on a curve (FIG. 5b).

On the death of the mice, the tibias are dissected and analysed in tomography by µCT scanner. The number of trabeculae per millimeter is measured by the method described in Hildebrand et al 1997 (FIG. 5d).

The liver cells are sampled, fixed in paraformaldehyde at 4° C., included in paraffin and analysed under confocal microscopy after marking of the chromatin with DAPI (4'6-diamidino-2-phenylindole). The percentage of abnormal nuclei is estimated by counting (FIG. 5e).

The survival of the treated mice is greatly improved, and is maximum in particular for females, with an extension of the average length of life by approximately 80% (FIG. 5c) The clinical symptoms of illness are all considerably reduced compared with the individuals treated with PBS alone.

REFERENCES

Basso A D, Kirschmeier P, Bishop W R. *Farnesyl transferase inhibitors*. J Lipid Res 47:15-31, 2006.

Biamonti G, Giacca M, Perini G, Contreas G, Zentilin L, Weighardt F, Guerra M, Della Valle G, Saccone S, Riva S et al. The *gene for a novel human lamin maps at a highly transcribed locus of chromosome 19 which replicates at the onset of S-phase*. Mol Cell Biol 12:3499-3506, 1992.

Bishop W R, Kirschmeier P, Baun C. *Farnesyl transferase inhibitors: mechanism of action, translational studies and clinical evaluation*. Cancer Biol Ther 2:S96-104, 2003.

Broers J L, Hutchinson C J, Ramaekers F C. *Laminopathies*. J Pathol 204:478488, 2004.

Broers J L V, Ramaekers F C S, Bonne G, Ben Yaou R, Hutchinson C J. *Nuclear lamins: laminopathies and their role in premature aging*. Physiol Rev 86:9671008, 2006.

Cadinanos J, Varela I, Lopez-Otin C, Freije J M. *From immature lamin to premature aging: molecular pathways and therapeutic opportunities.* Cell Cycle 4:1732-1735, 2005.

Capell B C, Erdos M R, Madigan J P, Fiordalisi J J, Varga R, Conneely K N, Gordon L B, Der C J, Cox A D, Collins F S. *Inhibiting farnesylation of progerin prevents the characteristic nuclear blebbing of Hutchinson-Gilford progeria syndrome.* Proc Natl Acad Sci USA 102:12879-12884, 2005.

De Sandre-Giovannoli A, Bernard R, Cau P, Navarro C, Amiel J, Boccaccio I, Lyonnet S, Stewart C L, Munnich A, Le Merrer M, Levy N. *Lamin A truncation in Hutchinson-Gilford progeria.* Science 300:2055, 2003, Demyanets S, Kaun C, Pfaffenberger S, Philipp J. Hohensinner P J, Rega G, Pammer J, Maurer G, Huber K, Wojta J. *Hydroxymethylglutatyl-coenzyme A reductase inhibitors induce apoptosis in human cardiac myocytes in vitro.* Biochem Pharmacol 71:1324-1330, 2006.

Duque G, Rivas D. *Age-related changes in Lamin A/C expression in the osteoarticular system: laminopathies as a potential new aging mechanism.* Mech Aging Dev 127: 378-383, 2006.

Efuet E T, Keyomarsi K. *Farnesyl and geranylgeranyl transferase inhibitors induce GI arrest by targeting the proteasome.* Cancer Res 66:1040-1051, 2006.

Eriksson M, Brown W T, Gordon L B, Glynn M W, Singer J, Scott L, Erdos M R, Robbins C M, Moses T Y, Berglund P, Dutra A, Pak E, Durkin S, Csoka A B, Boehnke M, Glover T W, Collins F S. *Recurrent de novo point mutation in lamin A cause Hutchinson-Gilford progeria syndrome.* Nature 423:293-298, 2003.

Evans M, Rees A. The *myotoxicity of statins.* Cur Op Lipid, 13:415-420, 2002.

Flint O P, Masters B A, Gregg R E, Durham S K. *HMG CoA reductase inhibitor-induced myotoxicity: pravastatin and lovastatin inhibit the geranylgeranylation of low-molecular-weight proteins in neonatal rat muscle cell culture.* Tox Appl Pharmacol 145:99-110, 1997.

Fong L G, Frost D, Meta M, Qiao X, Yang S H, Coffinier C, Young S G. *A protein farnesyltransferase inhibitor ameliorates disease in a mouse model of progeria.* Science, 311: 1621-1623, 2006.

Fong L G, Ng J K, Lammerding J, Vickers T A, Meta M, Coté N, Gavino B, Qiao X, Chang S Y, Young S R, Yang S H, Stewart C L, Lee R T, Bennett C F, Bergo M O, Young S G. *Prelamin A and Lamin A appear to be dispensable in the nuclear lamina.* J Clin Invest 116:743-752, 2006.

Fong L G, Ng J K, Meta M, Cote N, Yang S H, Stewart C L, Sullivan T, Burghardt A, Majumdar S, Reue K, Bergo M O, Young S G. *Heterozygosity for Lmna deficiency eliminates the progeria-like phenotypes in Zmpste24deficient mice.* Proc Natl Acad Sci USA 101:18111-18116, 2004.

Glynn M W, Glover T W. Incomplete processing of *mutant lamin A in Hutchison-Gilford progeria leads to nuclear abnormalities, which are reversed by farnesyltransferase inhibition.* Hum Mol Genet 14:2959-2969, 2005.

Goldman R D, Shumaker D K, Erdos M R, Eriksson M, Goldman A E, Gordon L B, Gruenbaum Y, Khuon S, Mendez M, Varga R, Collins F S. *Accumulation of mutant lamin A causes progressive changes in nuclear architecture in Hutchinson-Gilford progeria syndrome.* Proc Natl Acad Sci USA 101:89638968, 2004.

Gruenbaum Y, Margalit A, Goldman R D, Shumaker D K, Wilson K L. *The nuclear lamina comes of age.* Nat Mol Cell Biol 6:21-31, 2005.

Gruenbaum Y, Wilson K L, Harel A, Goldberg M, Cohen M. *Review: nuclear lamins—structural proteins with fundamental functions.* J Struct Biol 129:313323, 2000.

Hampton R, Dimster-Denk D, Rine J. *The biology of HMG-CoA reductase: the pros of contra-regulation.* Trends Biochem Sci 21:140-145, 1996.

Harborth J, Elbashir S M, Bechert K, Tuschl T, Weber K. *Identification of essential genes in cultured mammalian cells using small interfering RNAs.* J Cell Sci 114:4557-4565, 2001.

Hegele R A, Cao H, Liu D M, Costain G A, Charlton-Menys V, Rodger N W, Durrington P N. *Sequencing of reannotated LMNB2 gene reveals novel mutations in patients with acquired partial lipodystrophy.* Am J Hum Genet 79:383-389, 2006.

Hildebrand T, Ruegsegger P. *A new method for the model independent assessment of thickness in three dimensional images.* J Microsc 185:67-75, 1997.

Hoffmann G F, Charpentier C, Mayatepek E, Mancini J, Leichsenring M. Gibson K M, Divry P. Hrebicek M, Lehnert W, Sartor K. *Clinical and biochemical phenotype in 11 patients with mevalonic aciduria.* Pediatrics 91:915-921, 1993.

Huang S, Chen L, Libina N, Janes J, Martin G M, Campisi J, Oshima J. *Correction of cellular phenotypes of Hutchinson-Gilford Progeria cells by RNA interference.* Hum Genet. 2005 Oct. 6:1-7

Hutchinson C J, Worman H J. *A-type lamins: guardians of the soma?* Nat Cell Biol 6:1062-1067, 2004.

Ji J Y, Lee R T, Vergnes L, Fong L G, Stewart C L, Reue K, Young S G, Zhang Q, Shanahan C M, Lammerding J. Cell *nuclei spin in the absence of Lamin B1*, J Biol Chem online, Aug. 5, 2007.

Kusuyama T, Omura T, Nishiya D, Enomoto S, Matsumoto R, Murata T, Takeuchi K, Yoshikawa J, Yoshiyama M. *The effects of HMG-CoA reductase inhibitor on vascular progenitor cells.* J Pharmacol Sci 1001:344-349, 2006.

Leung K F, Baron R, Seabra M C. *Geranylgeranylation of Rab GTPases.* J Lipid Res 47:467-475, 2006.

Lévy N, Cau P. *Anomalies du noyau et maladies.* Pour la Science 313:2-7, 2003.

Lin F, Worman H J. *Structural organization of the human gene (LMNB1) encoding nuclear lamin B1.* Genomics 27:230-236, 1995.

Lin F, Woman H J. *Structural organization of the human gene encoding nuclear lamin A and nuclear lamin C.* J Biol Chem 268:16321-16326, 1993.

Maraldi N M, Squarzoni S, Sabatelli P, Capanni C, Mattioli E, Ognibene A, Lattanzi G. *Laminopathies: involvement of structural nuclear proteins in the pathogenesis of an increasing number of human diseases.* J Cell Physiol 203: 319-327, 2005.

Mattout A, Dechat T, Adam S A, Goldman R D, Gruenbaum Y. *Nuclear lamins, diseases and aging.* Cur Op Cell Biol 18:335-341, 2006.

Navarro C L, Cadinanos J, De Sandre-Giovannoli A, Bernard R, Courrier S, Boccaccio I, Boyer A, Kleijer W J, Wagner A, Giuliano F, Beemer F A, Freije J M, Cau P, Hennekam R C, Lopez-Otin C, Badens C, Levy N. *Loss of ZMPSTE24 (FACE-1) causes autosomal recessive restrictive dermopathy and accumulation of Lamin A precursors.* Hum Mol Genet 14:1503-1513, 2005.

Navarro C L, De Sandre-Giovannoli A, Bernard R, Boccaccio I, Boyer A, Genevieve D, Hadj-Rabia S, Gaudy-Marqueste C, Smitt H S, Vabres P, Faivre L, Verbes A, Van Essen T, Flori E, Hennekam R, Beemer F A, Laurent N, Le Merrer M, Cau P, Levy N. *Lamin A and ZMPSTE24 (FACE-1)* defects cause nuclear disorganization and identify restrictive dermopathy as a lethal neonatal laminopathy. Hum Mol Genet 13:2493-2503, 2004.

Padiath Q S, Saigoh K, Schiffmann R, Asahara H, Yamada T, Koeppen A, Hogan K, Ptacek L J, Fu Y H. *Lamin B1 duplications cause autosomal dominant leukodystrophy.* Nature Genet 38:1114-1123, 2006.

Pendas A M, Zhou Z, Cadinanos J, Freije J M, Wang J, Hultenby K, Astudillo A, Wernerson A, Rodriguez F, Tryggvason K, Lopez-Otin C. *Defective prolamin A processing and muscular and adipocyte alterations in Zmpste24 metalloproteinase-deficient mice.* Nat Genet 31:94-99, 2002.

Reid T S, Terry K L, Casey P J, Beese L S. *Crystallographic analysis of CaaX prenyltransferases complexed with substrates defines rules of protein substrate selectivity.* J Mol Biol 343:417-433, 2004.

Robber R A, Weber K, Osborn M. *Differential timing of nuclear lamin A/C expression in the various organs of the mouse embryo and the young animal: a developmental study.* Development 105:365-378, 1989.

Scaffidi P, Misteli T. *Lamin A-dependent nuclear defects in human aging.* Sciencexpress, 27 avril 2006.

Scaffidi P, Misteli T. *Reversal of the cellular phenotype in the premature aging disease Hutchinson-Gilford progeria syndrome.* Nat Med 11:440-445, 2005.

Scaffidi P, Misteli T. *Reversal of the cellular phenotype in the premature aging disease Hutchinson-Gilford progeria syndrome.* Nature Med 11:440-445, 2005.

Shelton K R, Egle P M, Cochran D L. *Nuclear envelope proteins: identification of lamin B subtypes.* Biochem Biophys Res Comm 103:975-981, 1981, Shumaker D K, Kuczmarski E R, Goldman R D. *The nucleoskeleton: lamins an actin are major players in essential nuclear functions.* Curr Op Cell Biol 15:358-366, 2003.

Stewart C, Burke B. *Teratocarcinoma stem cells and early mouse embryos contain only a single major lamin polypeptide closely resembling lamin B.* Cell 51:383-392, 1987.

Takedaa M, Noshiroa R, Onozatob M L, Tojob A, Hasannejada H, Huangc X L, Narikawac S, Endoua H. *Evidence for a role of human organic anion transporters in the muscular side effects of HMG-CoA reductase inhibitors.* Eur J Pharm 483:133-138, 2004.

Toth J I, Yang S H, Qiao X. Beigneux A P, Gelb M H, Moulson C L, Miner J H, Young S G, Fong L G. *Blocking protein farnesyltransferase improves nuclear shape in fibroblasts from humans with progeroid syndromes.* Proc Natl Acad Sci USA 102:12873-12878, 2005.

Tsai M Y, Wang S, Heidinger J M, Shumaker D K, Adam S A, Goldman R D, Zheng Y. *A mitotic lamin B matrix induced by RanGTP required for spindle assembly.* Science 311: 1887-1893, 2006.

Varela I, Cadinanos J, Pendas A M, Gutierrez-Fernandez A, Folgueras A R, Sanchez L M, Zhou Z, Rodriguez F J, Stewart C L, Vega J A, Tryggvason K, Freije J M, Lopez-Otin C. *Accelerated aging in mice deficient in Zmpste24 protease is linked to p53 signaling activation.* Nature 437: 564-568, 2005.

Vergnes L, Peterfy M, Bergo M O, Young S G, Reue K. *Lamin B1 is required for mouse development and nuclear integrity.* Proc Natl Acad Sci USA 101:10428-10433, 2004.

Winter-Vann A M, Casey P J. *Post-prenylation-processing enzymes as new targets in oncogenesis.* Nat Rev Cancer 5:405-412, 2005.

Wydner K L, McNeil J A, Lin F, Worman H J, Lawrence J B. *Chromosomal assignment of human nuclear envelope protein genes LMNA, LMNB1 and LBR by fluorescence in situ hybridization.* Genomics 32:474-478, 1996.

Young S G, Meta M, Yang S H, Fong L G. *Prelamin A farnesylation and progeroid syndromes.* J Biol Chem 281: 39741-39745, 2006.

Zastrow M S, Vlcek S, Wilson K L. *Proteins that bind A-type lamins: integrating isolated clues.* J Cell Sci 117:979-987, 2004.

Zhang F L, Casey P J. *Protein prenylation: molecular mechanisms and functional consequences.* Annu Rev Biochem 65:241-269, 1996.

The invention claimed is:

1. A method of treating Progeria or restrictive dermopathy, the method comprising administering to a subject in need thereof, a synergistically effective amount of a combination of pravastatin or a pharmaceutically acceptable salt thereof and zoledronic acid or zoledronate or a pharmaceutically acceptable salt thereof.

2. A method of inhibiting the abnormal accumulation of prenylated protein in cells of a subject, the method comprising administering to said subject a synergistically effective amount of the combination of pravastatin or a pharmaceutically acceptable salt thereof and zoledronic acid or zoledronate or a pharmaceutically acceptable salt thereof.

3. The method of claim 2, further comprising administering to said subject at least one HMG-CoA inhibitor that is not pravastatin or a pharmaceutically acceptable salt thereof and/or optionally further comprising at least one farnesyl-pyrophosphate synthase inhibitor that is not zoledronic acid or zoledronate or a pharmaceutically acceptable salt thereof.

4. The method of claim 2, wherein said prenylated protein is farnesylated and/or geranylgeranylated protein.

5. The method of claim 2, wherein the subject has Progeria or restrictive dermopathy.

* * * * *

UNITED STATES PATENT AND TRADEMARK OFFICE
CERTIFICATE OF CORRECTION

PATENT NO. : 8,518,914 B2  
APPLICATION NO. : 12/307220  
DATED : August 27, 2013  
INVENTOR(S) : Nicolas Levy et al.

Page 1 of 1

It is certified that error appears in the above-identified patent and that said Letters Patent is hereby corrected as shown below:

Title Page

Item (73) - please correct the first Assignee to read as follows:

--Université d'Aix-Marseille--

Signed and Sealed this
Twenty-fifth Day of February, 2014

Michelle K. Lee
*Deputy Director of the United States Patent and Trademark Office*